United States Patent [19]

Hetz et al.

[11] 4,110,723
[45] Aug. 29, 1978

[54] ULTRASONIC APPARATUS FOR MEDICAL DIAGNOSIS

[76] Inventors: Walter Hetz, Adam-Kraftstr. 17; Richard Soldner, Hedenusstr. 31, both of 8520 Erlangen, Germany

[21] Appl. No.: 557,384

[22] Filed: Mar. 11, 1975

[30] Foreign Application Priority Data

Mar. 27, 1974 [DE] Fed. Rep. of Germany ....... 2414777

[51] Int. Cl.² ............................................. G01S 9/66
[52] U.S. Cl. .................................... 340/1 R; 73/620; 340/8 FT
[58] Field of Search ..................... 340/1 R, 8 FT, 8 S; 73/67.8 S

[56] References Cited
U.S. PATENT DOCUMENTS 3,470,868  10/1969  Krause et al. ................. 340/8 FT X

*Primary Examiner*—Richard A. Farley

[57] ABSTRACT

An ultrasonic apparatus for medical diagnosis operating in accordance with the impulse-echo method, which includes a cylindrical parabola reflector and at least one ultrasonic transducer rotatably positioned in the focal line thereof for the transmission and receipt of ultrasonic signals, the latter of which being so constructed that the ultrasonic beam transmitted thereby after reflection at the reflector, is displaced during its rotation in a plane parallel in the sense of a line-by-line image build-up, and wherein the current receiving direction coincides with the transmission direction. The reflector, in conjunction with the ultrasonic transducer, is supported so as to be pivotable about a transverse axis, which is so oriented that by means of tilting or inclining of the reflector there may be scanned various object section planes.

4 Claims, 3 Drawing Figures

ULTRASONIC APPARATUS FOR MEDICAL DIAGNOSIS

FIELD OF THE INVENTION

The present invention relates to an ultrasonic apparatus for medical diagnosis operating in accordance with the impulse-echo method, which includes a cylindrical parabola reflector and at least one ultrasonic transducer rotatably positioned in the focal line thereof for the transmission and receipt of ultrasonic signals, the latter of which being so constructed that the ultrasonic beam transmitted thereby, after reflection at the reflector, is displaced during its rotation in a plane parallel in the sense of a line-by-line image build-up, and wherein the current receiving direction coincides with the transmission direction.

DISCUSSION OF THE PRIOR ART

In a known ultrasonic apparatus of the above-mentioned type, two ultrasonic transducers are fastened onto a common carrier or support which is rotatable about an axis formed by the focal line of a cylindrical parabola reflector and displaceable along the direction of the focal line of the parabola reflector. Thereby, the particular ultrasonic transducer which transmits in the direction away from the reflector, is temporarily suspended from operation. The displacement of the ultrasonic transducer along the direction of the focal line of the reflector has the effect that there may be encompassed a plurality of mutually parallel located sectional planes of the examined tissue area, without requiring any displacement of the entire ultrasonic apparatus with respect to the patient.

However, a disadvantage of the known ultrasonic apparatus lies in that, due to the necessary displacement of the carrier for the ultrasonic transducer along the direction of the focal line of the ultrasonic reflector, there must be provided a relatively extensive adjusting mechanism, which requires large amount of space within the apparatus and wherein, furthermore, the reflector must be so dimensioned in its physical size as to afford a satisfactory scanning of the examined tissue area over the entire adjusting range of the carrier for the ultrasonic transducer, the ultrasonic reflector thus needing to be constructed relatively high and, consequently, assuming a large amount of space.

SUMMARY OF THE INVENTION

Accordingly, it is an object of the present invention to provide an ultrasonic apparatus of the above-mentioned type, which is considerably simplified in construction as compared to the current state of the technology and wherein, in particular, the spatial requirements for the adjusting mechanism for the setting of different sectional planes and the spatial requirements for the ultrasonic reflector are much lower than for those in the known ultrasonic apparatus.

The foregoing object is inventively achieved in that the reflector, in conjunction with the ultrasonic transducer, is supported so as to be pivotable about a transverse axis, is so oriented that by means of tilting or inclining of the reflector there may be scanned various object section planes. In the inventive ultrasonic apparatus, for effecting a change in the section plane, it is not the carrier for the ultrasonic transducer which is displaced along the direction of the focal line of the ultrasonic reflector, but the ultrasonic deflector is tilted about a transverse axis which preferably extends in perpendicular to its focal line and its symmetry plane and, namely, at a distance to the focal line.

This transverse axis may also extend approximately in parallel with the surface which is defined by the ultrasonic outlet and inlet apertures of the housing within which the reflector is located. Since no displacement of the carrier for the ultrasonic transducer is effected along the direction of the focal line of the reflector so that the ultrasonic beam practically always traverses the same region of the reflector, this reflector may be essentially constructed smaller then that of the known ultrasonic apparatus. Further, this adjusting mechanism requires essentially less space and is simpler in its construction than the adjusting mechanism for the carrier of the ultrasonic transducer used in the known ultrasonic apparatus.

In an ultrasonic apparatus, wherein the aperture of the reflector housing is closed off through the intermediary of a foil formed of flexible material including a surface adapted to be applied to a patient, and in which the space between the reflector and foil is fitted with water, an embodiment of the invention consists of in that the foil is constituted of a unitary, hood-shaped component which is fastened to the aperture of the reflector housing and encompassed by a stiff guide sleeve from which it projects with its free end, which incorporates the application surface. Thereby, the occurrence of error signals resulting from reflections at housing portions are extensively avoided. If a suitable type of rubber is utilized for the foil component which is positioned on the reflector housing, then at the border or contact surface between the water which is employed for sound transmission and the rubber surface, there occurs practically no reflections due to the approximately equal sound velocities and densities in both of these media. The reflections at the surface of the rubber component contacting the air are damped in the rubber itself to such an extent due to its high sound absorption, so as not to be able to influence the image in any undesirable manner. The component is so constructed and conformed to the reflector housing, that the reflections at the housing portions which could conceivably cause errors in the sectional image, are extensively suppressed.

BRIEF DESCRIPTION OF THE DRAWING

Further advantages and details of the invention may now be ascertained from the following description of an exemplary embodiment thereof, taken in conjunction with the accompanying drawing, in which.

DETAILED DESCRIPTION

Figure 1:
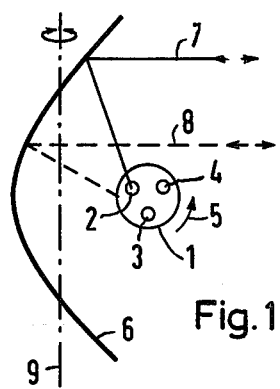
FIG. 1 shows, in plan view, a schematic representation of an ultrasonic apparatus pursuant to the present invention.
Figure 2:
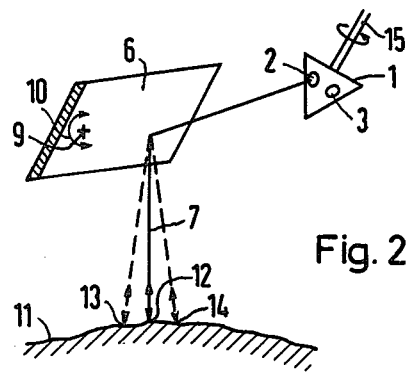
FIG. 2 shows a top plan view of the apparatus.

Referring now to the embodiment illustrated in FIGS. 1 and 2 of the drawing, a carrier 1, which supports three ultrasonic transmitting and receiving transducers 2 through 4 which are offset by about 120° relative to each other, is rotated in the direction of arrow 5, or in the opposite direction. At any one time, one of the transducer heads 2 through 4 projects an ultrasonic beam onto an ultrasonic parabola reflector 6. The carrier 1 is located in the focal line of the parabola reflector 6 so that the transmitted and received ultrasonic beam from the particular ultrasonic transducer 2 through 4, upon rotation of the carrier 1, is displaced in parallel within a plane subsequent to reflection by reflector 6 in the sense of a line-by-line image build-up. This is clarified in FIG. 1, in that the ultrasonic beam is illustrated for two different representative positions of the carrier 1, and respectively designated by 7 and 8. The present receiving direction coincides with the transmission direction. The up to now described arrangement facilitates the scanning of a sectional plane of a body by means of ultrasonics and to produce a sectional image represented on a viewing apparatus. If another sectional plane is to be selected without changing the position of the ultrasonic apparatus with respect to the examined body, then the ultrasonic reflector 6, together with the transducer axis, is tilted about axis 9. The foregoing is more clearly elucidated with respect to FIG. 2 of the drawing.

FIG. 2 illustrates the arrangement according to FIG. 1, taken in a side view. The parabola reflector 6 is shown partly in section. The axis 9 passes through the parabola reflector 6 perpendicular to the plane of symmetry thereof and thereby to the drawing plane, and the parabola reflector 6, together with the transducer axis, is pivotable about this axis in the direction of arrow 10. The examined body 11, in the illustrated position of the reflector, is impinged upon by the ultrasonic beam 7 at the location 12. Similarly, at this location, the outgoing reflected ultrasonic vibrations are again received by the currently actuated ultrasonic transducer (in the illustrated position transducer 2). Should the position of the sectional plane be changed, then as mentioned, the parabola reflector 6, together with its transducer axis, is somewhat tilted about the axis 9 in the direction of arrow 10. If this tilting is effected in a clockwise direction, then the beam 7 is so deflected as to impinge against the body 11 at location 13. If the tilting is effected in a counter clockwise direction, then the ultrasonic beam contacts at the location 14. In correspondence with the current position of the parabola reflector 6, there are thus encompassed different sectional planes of the examined body 11.

In FIG. 2 there further is illustrated the rotational axis 15 of the carrier 1 for the ultrasonic transducers 2 through 4. This rotational axis coincides with the focal line of the parabola reflector 6.

Figure 3:
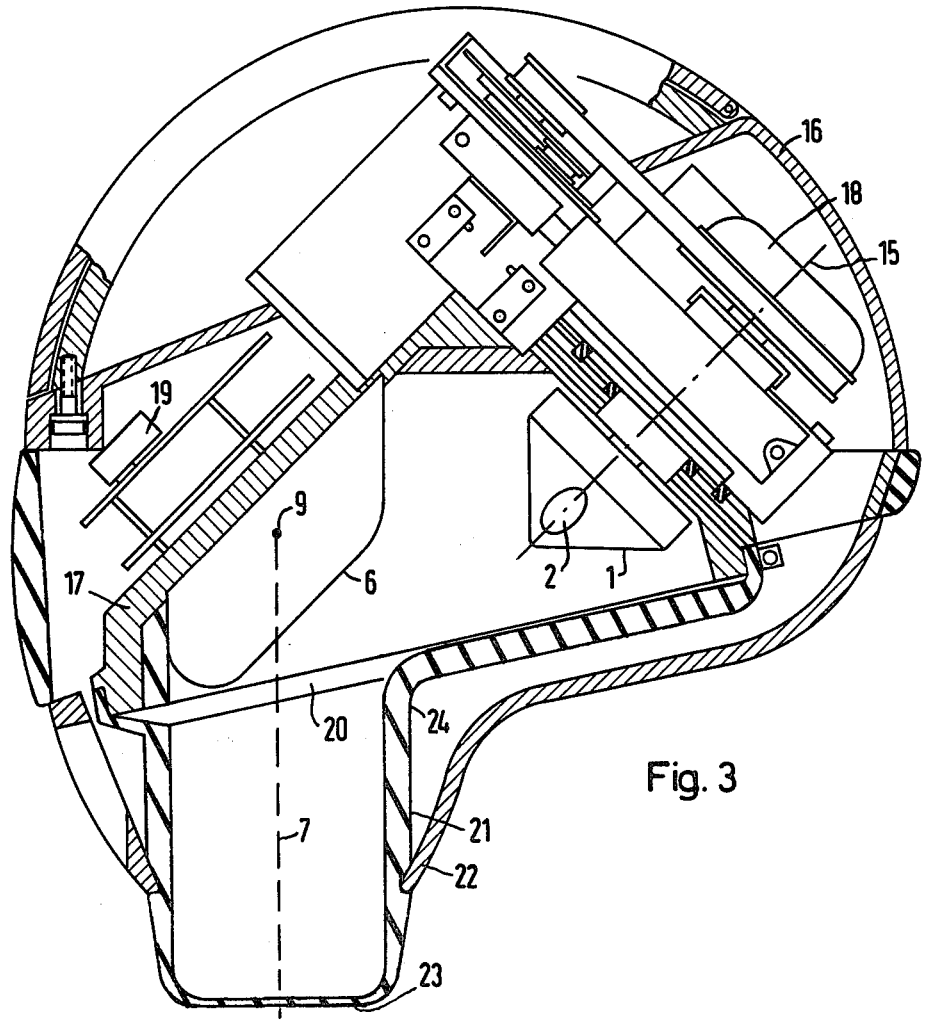
FIG. 3 shows a sectional view through an ultrasonic apparatus constructed pursuant to the invention.

The sectional view taken in FIG. 3 illustrates the housing 16 of the ultrasonic apparatus, within which there is supported the reflector housing 17 so as to be pivotable about axis 9. Within housing 17 there may be ascertained the reflector 6. The carrier 1 is rotatably supported in housing 17 and is rotated about axis 15 by means of a drive mechanism 18, the latter of which is only schematically illustrated. A motor 19 serves for effecting the pivoting of the housing 17 with the ultrasonic reflector 6.

The reflector housing 17 includes an outlet or, respectively, inlet aperture 20 for the ultrasonic radiation, to which there is fastened a cap or hood-shaped component 21 fully covering this aperture. The component 21 is encompassed by a rigid guide sleeve 22, which is a portion of the apparatus housing 16, or is fixedly connected therewith. The component 21 projects with its free end 23 from the guide sleeve 22, and is adapted to have this end contact the patient being examined. The reflector housing 17 and the component are filled with water which, in a known manner, serves as a sound transmitting medium.

If the reflector housing 17, together with the reflector 6 and the focal axis 9 is to be pivoted about axis 9, then the motor 19 must be actuated. The pivoting is possible since the component 21 is yieldable relative to the guide sleeve 22 or, respectively, the housing 16. The component 21 is bent at location 24 and covers the entire opening of the reflector housing 17. Ultrasound is practically not reflected at the border between the water and the component 21, which consists of rubber, since the speed of sound and density in both of these media are approximately equally large. Reflections occur in all instances at the outer surface of the component 21, which borders on air, however, these reflections are absorbed in the relatively thick wall portions of the component 21 and do not disturb the ultrasonic image.

Within the scope of the invention it is not important as to the number of ultrasonic transducers which may be fastened to the carrier 1. Thus, there may be located thereon, in effect, only one ultrasonic transducer, or there may be provided two ultrasonic transducers. The aperture of the reflector 6 must be dimensioned in conformance with the number of ultrasonic transducers. Only one ultrasonic beam of any one ultrasonic head always impinges against the reflector.

While there has been shown what is considered to be the preferred embodiment of the invention, it may be obvious that modifications may be made which come within the scope of the disclosure of the specification.

What is claimed is:

1. In an ultrasonic apparatus for medical diagnosis operating pursuant to the impulse-echo method, including a cylindrical parabola reflector; at least one ultrasonic transducer rotatably positioned in the focal line of said reflector for the transmission and receipt of ultrasonic signals; and means for displacing the ultrasonic beam transmitted from said transducer upon rotation thereof in a parallel plane after reflection by said reflector in the context of a line-by-line image build-up, wherein the current receiving direction coincides with the transmission direction, the improvement comprising: means supporting said parabola reflector and said ultrasonic transducer for pivotable motion about a transverse axis, said transverse axis being oriented to facilitate the scanning of different object sectional planes responsive to tilting of said reflector; a housing having an inlet and outlet aperture for the ultrasonic radiation, said reflector being located in said housing, said ultrasonic transducer being rotatably supported on said housing; a further housing encompassing said ultrasonic apparatus, said reflector housing being pivotably supported within said further housing.

2. An apparatus as claimed in claim 1, comprising an electrical motor between said reflector housing and the housing for said ultrasonic apparatus for effecting said pivoting motion therebetween.

3. An apparatus as claimed in claim 1, comprising a foil formed of a flexible material having an application surface being connected to said reflector housing for closing off said aperture so as to form a space between said reflector and said foil, said space being filled with water, said foil being a portion of a unitary hood-shaped component fastened to said reflector housing aperture; and a rigid guide sleeve encompassing said component, the free end of said foil having said application surface projecting beyond said guide sleeve.

4. An apparatus as claimed in claim 3, said guide sleeve and the housing of said ultrasonic apparatus containing said reflector housing forming a rigid unitary structure.

* * * * *